United States Patent [19]

Ohsaka et al.

[11] Patent Number: 4,825,014

[45] Date of Patent: Apr. 25, 1989

[54] PROCESS FOR PREPARING CHLOROTRIFLUOROMETHYLBENZENE

[75] Inventors: Yohnosuke Ohsaka; Heikitsu Sonoyama, both of Osaka, Japan

[73] Assignee: Daikin Kogyo Co., Ltd., Osaka, Japan

[21] Appl. No.: 206,664

[22] Filed: Jun. 15, 1988

Related U.S. Application Data

[63] Continuation of Ser. No. 414,045, Sep. 2, 1982, abandoned.

[30] Foreign Application Priority Data

Sep. 3, 1981 [JP] Japan ................................ 56-139442
Oct. 15, 1981 [JP] Japan ................................ 56-165460
Nov. 10, 1981 [JP] Japan ................................ 56-181471

[51] Int. Cl.$^4$ ........................ C07C 17/14; C07C 21/24
[52] U.S. Cl. ..................................... 570/144; 502/224; 502/227; 502/228; 502/229
[58] Field of Search .......................................... 570/144

[56] References Cited

U.S. PATENT DOCUMENTS

| | | | |
|---|---|---|---|
| 3,187,060 | 6/1965 | Petit et al. | 252/442 |
| 4,012,337 | 3/1977 | Mitchell | 252/442 |
| 4,242,286 | 12/1980 | Ohsaka | 570/145 |
| 4,365,101 | 12/1982 | Nakagawa et al. | 570/145 |
| 4,367,350 | 1/1983 | Hiramatsu et al. | 570/145 |
| 4,436,942 | 3/1984 | Rader et al. | 570/145 |

Primary Examiner—J. E. Evans
Attorney, Agent, or Firm—Birch, Stewart, Kolasch & Birch

[57] ABSTRACT

Chlorotrifluoromethylbenzene is prepared with a good yield by reacting chlorotoluene, hydrogen fluoride and chlorine in a gaseous phase in the presence of a catalyst selected from the group consisting of α-aluminum fluoride, α-aluminum fluoride carrying one or more salts of iron, bismuth, tin and lead, and chromium(III) oxide or partially fluorinated chromium(III) oxide carrying alkali metal fluoride.

12 Claims, No Drawings

PROCESS FOR PREPARING CHLOROTRIFLUOROMETHYLBENZENE

This application is a continuation of copending application Ser. No. 414,045, filed on Sept. 2, 1982, now abandoned.

BACKGROUND OF THE INVENTION

This invention relates to a process for preparing chlorotrifluoromethylbenzene. More particlarly, it relates to a process for preparing chlorotrifluoromethylbenzene by reacting chlorotoluene, hydrogen fluoride and chlorine in a gaseous phase in the presence of a certain specific catalyst.

Chlorotrifluoromethylbenzene is a known compound and useful as an intermediate in the production of medicines, dyes, agricultural chemicals, and the like.

For the production of p-chlorotrifluoromethylbenzene, there are known several processes including a process comprising reacting p-chlorotrichloromethylbenzene with hydrogen fluoride in the presence of aluminum fluoride (cf. Japanese Patent Publication (unexamined) No. 13052/1979) and a process comprising reacting p-chlorotoluene with chlorine and hydrogen fluoride in a gaseous phase at an elevated temperature (cf. Japanese Patent Publication (unexamined) No. 82728/1978). The latter process is superior to the former process since the starting material, i.e. p-chlorotrichloromethylbenzene, in the former process is prepared by chlorinating p-chlorotoluene. The latter process, however, has some disadvantages such that the reaction temperature is high and the selectivity is low.

SUMMARY OF THE INVENTION

As a result of an extensive study on catalysts which are useful in the production of chlorotrifluoromethylbenzene by reacting chlorotoluene, hydrogen fluoride and chlorine, it has now been found that α-aluminum fluoride, α-aluminum fluoride carrying salts of iron, bismuth, tin and lead, and chrominum(III) oxide or partially fluorinated chromium(III) oxide carrying alkali metal fluoride are effective catalysts for the reaction and afford chlorotrifluoromethylbenzene with a good yield even at a low reaction temperature in a short reaction time.

DETAILED DESCRIPTION OF THE INVENTION

According to the present invention, there is provided a process for preparing chlorotrifluoromethylbenzene which comprises reacting chlorotoluene, hydrogen fluoride and chlorine in a gaseous phase in the presence of a catalyst selected from the group consisting of α-aluminum fluoride, α-aluminum fluoride carrying one or more salts of iron, bismuth, tin and lead, and chromium(III) oxide or partially fluorinated chromium(III) oxide carrying alkali metal fluoride.

α-Aluminum fluoride to be used in the process of the invention is a known compond (cf. Japanese Patent Publication No. 2252/1967). It may be prepared, for example, by heating aluminum fluoride, which may be anhydrous or hydrated and β-, γ-, δ- or ε- type or amorphous, at a temperature of not lower than 500° C. (e.g. 600° C.) for a period 5 to 7 hours, preferably under a nitrogen stream or a hydrogen fluoride stream. Aluminum fluoride may be prepared by treating activated alumina with hydrogen fluoride at a relatively low temperature, usually of from 200° to 350° C.

The salt to be used in the process of the invention may be carried on α-aluminum fluoride prepared as above by immersing the latter in a solution of the former in water or an aqueous solution of a volatile acid (e.g. hydrochloric acid) or a volatile base (e.g. aqueous ammonia). Specific examples of the salt solution are an aqueous solution of iron(III) chloride, a solution of bismuth(III) hydroxide in dilute hydrochloric acid, an aqueous solution of tin(II) chloride, an aqueous solution of lead(II) acetate or nitrate, or the like. After immersion, α-aluminum fluoride is heated at a temperature of from about 100° to 150° C. for about 2 to 24 hours and preferably treated with hydrogen fluoride under the reaction conditions.

The amount of the salt carried on 100 g of α-aluminum fluoride is usually from 0.0005 to 0.05 mole in the case of the salt of bismuth or from 0.001 to 0.1 mole in the of the salt of iron, tin or lead. When the amount is smaller than the lower limit, the catalytic effect of the carried salt is not sufficient. A larger amount than the upper limit is not economical.

Chromium(III) oxide may be prepared by treating a chromium(III) salt (e.g. chromium(III) chloride) with an alkali (e.g. aqueous ammonia) or by reducing a chromium(IV) compound (e.g. sodium bichromate) with sucrose, alcohols or aldehydes. Partially fluorinated chromium(III) oxide may be prepared by heating chromium(III) fluoride at a temperature of not lower than 350° C., for example, from 400° to 600° C. under oxygen stream (cf. U.S. Pat. No. 2,745,886) or by heating chromium(III) hydroxide at a temperature of not lower than 100° C., for example, from 150° to 500° C. under hydrogen fluoride stream (cf. Japanese Patent Publication No. 10601/1968).

Alkali metal fluoride may be carried on chromium(III) oxide or partially fluorinated chromium(III) oxide by immersing the latter in an aqueous solution of the former of a suitable concentration and drying the latter impregnated with the solution. When alkali metal fluoride has a low solubility in water such as sodium fluoride, instead of fluoride, a salt with an acid weaker than hydrofluoric acid (e.g. carbonate of the alkali metal or organic acid salts of the alkali metal such as sodium acetate) or hydroxide of the alkali metal is dissolved in water. Then, in the resulting solution, chromium(III) oxide or partially fluorinated chromium(III) oxide is immersed, dried and heated at a temperature of not lower than room temperature, preferably from 100° to 500° C., under hydrogen fluoride stream to obtain the catalyst.

Drying of chromium(III) oxide or partially fluorinated chromium(III) oxide after immersed in the solution of alkali metal fluoride, the salt of the alkali metal or hydroxide of the alkali metal may be effected by heating it at a temperature of from about 100° to 150° C. for a sufficient time of period, for example, about 2 to 24 hours.

The resulting chromium(III) oxide or partially fluorinated chromium(III) oxide carrying alkali metal fluoride as such can be used as a catalyst. Preferably, its catalytic activity is stabilized by keeping it in an atmosphere of hydrogen fluoride under a temperature and pressure condition similar to the reaction condition for 1 to 5 hours.

The amount of alkali metal fluoride carried on 100 g of chromium(III) oxide or partially fluorinated chromium(III) oxide is usually from 0.01 to 0.5 mole, preferably from 0.02 to 0.3 mole. When the amount is smaller than the lower limit, the catalytic effect of carried fluoride is not sufficient. When the amount is larger than the upper limit, the catalyst is expensive and its activity is deteriorated.

In the process of the invention, ammolar ratio of hydrogen fluoride to chlorotoluene is not critical. It is preferable to use a corresponding or slightly excess amount of hydrogen fluoride to hydrogen atoms to be substituted with fluorine atoms. The molar ratio is preferably from 3:1 to 30:1, more preferably from 4:1 to 20:1.

The molar ratio of chlorine to chlorotoluene is usually from 3:1 to 20:1, preferably from 4:1 to 15:1. When chlorine is less than the lower ratio, the reaction will hardly proceed. When chlorine is more than the upper ratio, no further advantage is obtained and a larger reactor is needed.

The reaction temperature may be usually from 250° to 450° C., preferably from 350° to 450° C. At a temperature lower than 250° C., the reaction rate is lower. At a temperature higher than 450° C., selectivity to the desired product is lower.

The reaction pressure is not critical. Usually a pressure of 0.5 to 10 atm., preferably of 1 to 3 atm. is employed.

The space velocity depends on the reaction temperature, the activity of the catalyst, and so forth. For example, at a reaction temperature of 400° C., the space velocity is from 200 to 4000 hr$^{-1}$, particularly from 200 to 2000 hr$^{-1}$. With a space velocity lower than 200 hr$^{-1}$, amounts of by-products increase. With a space velocity higher than 4000 hr$^{-1}$, the reaction rate decreases.

When the catalyst is deactivated after a long-term use, it can be reactivated by treating it with oxygen or oxygen-containing gas (e.g. air) at a temperature of from 400° to 500° C.

In the process of the invention, the raw materials may, if necessary, be diluted with a diluent gas such as nitrogen.

Any material to be used for the construction of the equipment including a reaction tube should resist corrosive gases (e.g. hydrogen fluoride, hydrogen chloride and chlorine) and is preferably stainless steel, nickel or nickel alloys (e.g. Inconel and Hastelloy).

The process of the invention may be carried out by passing a gaseous mixture of chlorotoluene, hydrogen fluoride and chlorine through a heated reactor containing the catalyst. The reaction in the process may be effected on a fixed bed as well as a fluidized bed. The raw materials are preferably preheated to vaporize them.

The reaction mixture discharged from the reactor is introduced in a distillation column. The condensed desired product is recovered from the bottom, and gaseous materials (e.g. hydrogen chloride, unreacted hydrogen fluoride and unreacted chlorine) are recovered from the top.

The term "yield" used herein means the molar ratio of resulting chlorotrifluoromethylbenzene to charged chlorotoluene, i.e. the product of conversion by selectivity.

PREFERRED EMBODIMENTS OF THE INVENTION

The present invention will be hereinafter explained in detail by the following Examples which are intended to illustrate, but not limit, the particulars of the present invention.

REFERENCE EXAMPLE 1

Activated alumina (50 g) with a particle size of 4 to 6 mm was charged into a Hastelloy-C (trade name) made reactor of ¾ inch in inner diameter and heated to 200° C. under nitrogen stream. Then, hydrogen fluoride was passed through the reactor at a flow rate of 200 ml/min. for 3.5 hours. After the movement of the hot spot finished, hydrogen fluoride was passed at the same rate, and the reactor was heated to 350° C. and kept at the same temperature for 3 hours. Then, the reactor was heated to 600° C. under hydrogen fluoride stream, kept at the same temperature for 7 hours and cooled. X-ray analysis showed that most of activated alumina was converted to α-aluminum fluoride.

EXAMPLE 1

Particulate α-aluminum fluoride (50 g) obtained in Reference Example 1 was charged into a Hastelloy-C (trade name) made reactor of ¾ inch in inner diameter and kept at 380° C. At the same temperature, a gaseous mixture of hydrogen fluoride, chlorine and p-chlorotoluene in a molar ratio of 10:10:1 was passed through the reactor with a space velocity of 274 hr$^{-1}$ at atmospheric pressure for 4 hours. The flow rate of p-chlorotoluene was 0.3 g/min. The reaction mixture discharged from the reactor was passed through an ice-cooled condenser, and a mixture of high-boiling materials was separated from resulting hydrogen chloride and unreacted hydrogen fluoride.

The condensed mixture of high-boiling materials including acidic materials was washed with water and dried over anyhydrous sodium sulfate. Crude p-chlorotrifluoromethylbenzene (105 g) was obtained. The results of gas-chromatographic analysis are shown in Table 1.

EXAMPLE 2

In the same manner as in Example 1 but using m-chlorotoluene in place of p-chlorotoluene, the reaction was carried out. Crude m-chlorotrifluoromethylbenzene (103 g) was obtained. The results of gaschromatographic analysis are shown in Table 1.

TABLE 1

| Example No. | Raw material | | Product | | By-product | Others |
|---|---|---|---|---|---|---|
| | p-CH$_3$-C$_6$H$_4$-Cl | m-CH$_3$-C$_6$H$_4$-Cl | p-CF$_3$-C$_6$H$_4$-Cl | m-CF$_3$-C$_6$H$_4$-Cl | p-CF$_3$-C$_6$H$_4$-Cl | |
| 1 | 0.0% | — | 76.8% | — | 9.0% | 14.2% |

TABLE 1-continued

| | Raw material | | Product | | By-product | |
|---|---|---|---|---|---|---|
| Example No. | CH₃-C₆H₄-Cl (para) | CH₃-C₆H₄-Cl (meta) | CF₃-C₆H₄-Cl (para) | CF₃-C₆H₄-Cl (meta) | CF₃-C₆H₄-Cl | Others |
| 2 | — | 0.0% | — | 26.0% | 4.5% | 69.5% |

Note: % is % by mole.

EXAMPLE 3

(1) α-Aluminum fluoride (50 ml, 53.10 g) obtained in Reference Example 1 was charged in a flask and kept at reduced pressure for 1 hour. Then, a solution of anhydrous iron(III) chloride (30 g) in water (50 g) was slowly added, stirred gently at reduced pressure for 1 hour and kept at reduced pressure for 3 hours. α-Aluminum fluoride (64.10 g) impregnated with the solution of iron(III) chloride was recovered by filtration and heated at 120° C. for 15 hours to obtain α-aluminum fluoride (53.68 g) carrying iron(III) chloride. The amount of carried iron(III) chloride calculated from the weight increment of α-aluminum fluoride was 0.048 mole per 100 g of α-aluminum fluoride. In the calculation, it was assumed that all iron(III) chloride in the impregnated solution had been carried on α-aluminum chloride, and variation of the concentration due to the evaporation of water was neglected.

(2) The thus obtained particulate α-aluminum fluoride (50 g) carrying the iron compound was charged into a Hastelloy-C (trade name) made reactor of ¾ inch in inner diameter and kept at 430° C. At the same temperature, a gaseous mixture of hydrogen fluoride, chlorine and p-chlorotoluene in a molar ratio of 12:5:1 was passed through the reactor with a space velocity of 970 hr$^{-1}$ at atmospheric pressure for 4 hours. The flow rate of p-chlorotoluene was 0.3 g/min. The reaction mixture discharged from the reactor was passed through an ice-cooled condenser, and a mixture of high-boiling materials was separated from resulting hydrogen chloride and unreacted hydrogen fluoride.

The condensed mixture of high-boiling materials including acidic materials was washed with water and dried over anhydrous sodium sulfate. Crude p-chlorotrifluoromethylbenzene (102 g) was obtained. The results of gaschromatographic analysis are shown in Table 2.

EXAMPLES 4 to 6

In the same manner as in Example 3(1) but using a solution of bismuth(III) hydroxide (30 g, 0.115 mole) in 4N-hydrochloric acid (98.8 g) (Example 4), a solution of bismuth(III) hydroxide (20 g, 0.077 mole) in 4N-hydrochloric acid (99.8 g) (Example 5) and a solution of bismuth(III) hydroxide (10 g, 0.038 mole) in 4N-hydrochloric acid (100 g), a catalyst was prepared. The amount of the bismuth compound carried on 100 g of α-aluminum fluoride was 0.018 mole, 0.013 mole and 0.007 mole respectively.

In the same manner as in Example 3(2) but using α-aluminum fluoride carrying the bismuth compound as a catalyst, the reaction was carried out. The crude product (104 g, 102 g and 102 g respectively) was obtained. The results of gaschromatographic analysis are shown in Table 2.

EXAMPLE 7

In the same manner as in Example 4 but evaporating off water and hydrogen chloride without filtrating α-aluminum fluoride impregnated with the solution of the bismuth compound, a catalyst was prepared. The amount of the bismuth compound carried on 100 g of α-aluminum fluoride was 0.145 mole.

In the same manner as in Example 3(2) but using the thus obtained catalyst, the reaction was carried out. The crude product (103 g) was obtained. The results of gaschromatographic analysis are shown in Table 2.

EXAMPLE 8

In the same manner as in Example 3(1) but using a solution of crystalline tin(II) chloride dihydrate (30 g, 0.133 mole) in water (50 g), a catalyst was prepared. The amount of the tin compound carried on 100 g of α-aluminum fluoride was 0.034 mole.

In the same manner as in Example 3(2) but using α-aluminum fluoride carrying the tin compound as a catalyst, the reaction was carried out. Crude p-chlorotrifluoromethylbenzene (102 g) was obtained. The results of gaschromatographic analysis are shown in Table 2.

EXAMPLE 9

In the same manner as in Example 3(1) but using a solution of lead(II) acetate (30 g, 0.092 mole) in water (50 g), a catalyst was prepared. The amount of the lead compound carried on 100 g of α-aluminum fluoride was 0.024 mole.

In the same manner as in Example 3(2) but using α-aluminum fluoride carrying the lead compound as a catalyst, the reaction was carried out. The crude product (103 g) was obtained. The results of gaschromatographic analysis are shown in Table 2.

EXAMPLE 10

In the same manner as in Example 4(2) but using m-chlorotoluene in place of p-chlorotoluene, the reaction was carried out. Crude m-chlorotrifluoromethylbenzene (102 g) was obtained. The results of gaschromatographic analysis are shown in Table 2.

TABLE 2

| Example No. | Carried metal (mole/100 g of α-AlF₃) | Raw material CH₃-⌬-Cl | Raw material CH₃-⌬-Cl (di) | Product CF₃-⌬-Cl | Product CF₃-⌬-Cl (di) | By-product CF₃-⌬-Cl-Cl | Others |
| --- | --- | --- | --- | --- | --- | --- | --- |
| 3  | Fe; 0.048 | 0.0% | —    | 82.8% | —     | 7.6% | 9.6%  |
| 4  | Bi; 0.018 | 0.0% | —    | 90.6% | —     | 4.7% | 4.7%  |
| 5  | Bi; 0.013 | 0.0% | —    | 81.3% | —     | 8.6% | 10.1% |
| 6  | Bi; 0.007 | 0.0% | —    | 80.2% | —     | 8.9% | 10.9% |
| 7  | Bi; 0.145 | 0.0% | —    | 87.0% | —     | 5.4% | 7.6%  |
| 8  | Sn; 0.034 | 0.0% | —    | 82.8% | —     | 5.3% | 11.9% |
| 9  | Pb; 0.024 | 0.0% | —    | 85.1% | —     | 8.2% | 6.7%  |
| 10 | Bi; 0.018 | —    | 0.0% | —     | 32.2% | 8.2% | 59.6% |

Note: % is % by mole.

REFERENCE EXAMPLE 2

Commercially available chromium(III) fluoride, trihydrate was shaped into pellets, each having a diameter of 6 mm and a length of 6 mm. The pellets (50 ml) were charged into a Hastelloy-C (trade name) made reactor of ¾ inch in inner diameter, heated to 500° C. over 30 minutes under air stream of 0.5 to 1 l/min. and kept at the same temperature under air stream for 2 hours. Then, the pellets were cooled to room temperature to obtain partially fluorinated chromium(III) oxide (hereinafter referred to as "chromium oxide A").

REFERENCE EXAMPLE 3

Chromium(III) hydroxide was shaped into pellets, each having a diameter of 6 mm and a length of 6 mm. The pellets (50 ml) were charged into a Hastelloy-C (trade name) made reactor, heated to 400° C. over 40 minutes under air stream of 200 ml/min. and kept at the same temperature for 2 hours. Then, the pellets were cooled to room temperature to obtain partially fluorinated chromium(III) oxide (hereinafter referred to as "chromium oxide B").

EXAMPLE 11

(1) Chromium oxide A (50 g) obtained in Reference Example 2 was charged in a flask and kept at reduced pressure for 1 hour. Then, a solution of potassium fluoride (15 g, 0.258 mole) in water (50 g) was slowly added, stirred gently at reduced pressure for 1 hour and kept at reduced pressure for 3 hours. Chromium oxide A (65.25 g) impregnated with the solution of potassium fluoride was recovered by filtration and heated at 120° C. for 15 hours to obtain chromium oxide A carrying potassium fluoride. The amount of potassium fluoride carried on 100 g of chromium oxide A was calculated to be 0.121 mole. The calculation was carried out in the same manner as in Example 3(1).

(2) The thus obtained chromium oxide A (50 ml) carrying potassium fluoride was charged into a Hastelloy-C (trade name) made reactor of ¾ inch in inner diameter and heated to 430° C. At the same temperature, hydrogen fluoride was passed through the reactor at a flow rate of 200 ml/min. for 2 hours. Then, at the same temperature, a gaseous mixture of hydrogen fluoride, chlorine and p-chlorotoluene in a molar ratio of 12:5:1 was passed through the reactor with a space velocity of 970 hr$^{-1}$ at atmospheric pressure. The flow rate of p-chlorotoluene was 0.3 g/min. The reaction mixture discharged from the reactor was passed through an ice-cooled condenser, and a mixture of high-boiling materials was separated from resulting hydrogen chloride and unreacted hydrogen fluoride.

The condensed mixture of high-boiling materials including acidic materials was washed with water and dried over anhydrous sodium sulfate. Crude p-chlorotrifluoromethylbenzene (105 g) was obtained. The results of gaschromatographic analysis are shown in Table 3.

EXAMPLES 12 and 13

In the same manner as in Example 11(1) but using 5 g (0.086 mole) of potassium fluoride (Example 12) and 98.4 g (1.194 mole) of potassium fluoride (Example 13) in place of 15 g of potassium fluoride, a catalyst was prepared. The amount of potassium fluoride carried on 100 g of chromium oxide A was 0.0476 mole and 0.348 mole respectively.

In the same manner as in Example 11(2) but using the thus obtained catalyst, the reaction was carried out. Crude p-chlorotrifluoromethylbenzene (103 g and 98 g respectively) was obtained. The results of gaschromatographic analysis are shown in Table 3.

EXAMPLE 14

In the same manner as in Example 11(1) but using cesium fluoride (10 g, 0.0658 mole) in place of potassium fluoride, a catalyst was prepared. The amount of cesium fluoride carried on 100 g of chromium oxide A was 0.0268 mole.

In the same manner as in Example 11(2) but using the thus obtained catalyst, the reaction was carried out. The crude product (102 g) was obtained. The results of gaschromatographic analysis are shown in Table 3.

EXAMPLE 15

In the same manner as in Example 11(1) but using anhydrous sodium carbonate (10 g, 0.0943 mole) in place of potassium fluoride, a catalyst was prepared. The amount of sodium carbonate carried on 100 g of chromium oxide A was 0.012 mole.

Pellets (50 ml) of chromium oxide A carrying sodium carbonate were charged into a Hastelloy-C (trade name) made reactor of ¾ inch in inner diameter and heated to 430° C. At the same temperature, hydrogen fluoride was passed through the reactor at a rate of 200 ml/min. for 2 hours to convert sodium carbonate into sodium fluoride. Thus, the amount of sodium fluoride carried on 100 g of chromium oxide A was 0.024 mole.

In the same manner as in Example 11(2) but using the thus obtained catalyst, the reaction was carried out. The crude product (101 g) was obtained. The results of gaschromatographic analysis are shown in Table 3.

EXAMPLE 16

In the same manner as in Example 11(1) but using chromium oxide B obtained in Reference Example 3 in place of chromium oxide A, a catalyst was prepared. The amount of potassium fluoride carried on 100 g of chromium oxide B was 0.113 mole.

In the same manner as in Example 11(2) but using the thus obtained catalyst, the reaction was carried out. The crude product (102 g) was obtained. The results of gaschromatographic analysis are shown in Table 3.

EXAMPLE 17

In the same manner as in Example 11(2) but using m-chlorotoluene in place of p-chlorotoluene, the reaction was carried out. Crude m-chlorotrifluoromethylbenzene (98 g) was obtained. The results of gaschromatographic analysis are shown in Table 3.

TABLE 3

| Example No. | Carried alkali metal fluoride (mole/100 g of chromium (III) oxide) | Raw material CH$_3$–C$_6$H$_4$–Cl (para) | Raw material CH$_3$–C$_6$H$_4$–Cl (meta) | Product CF$_3$–C$_6$H$_4$–Cl (para) | Product CF$_3$–C$_6$H$_4$–Cl (meta) | By-product CF$_3$–C$_6$H$_4$–Cl | Others |
|---|---|---|---|---|---|---|---|
| 11 | K; 0.121 | 0.0% | — | 82.6% | — | 4.5% | 12.9% |
| 12 | K; 0.0476 | 0.0% | — | 80.6% | — | 8.3% | 11.1% |
| 13 | K; 0.348 | 0.0% | — | 68.7% | — | 2.8% | 28.5% |
| 14 | Cs; 0.0268 | 0.0% | — | 79.4% | — | 8.7% | 11.9% |
| 15 | Na; 0.0240 | 0.0% | — | 80.2% | — | 8.0% | 11.8% |
| 16 | K; 0.113 | 0.0% | — | 81.9% | — | 4.3% | 13.8% |
| 17 | K; 0.121 | — | 0.0% | — | 30.8% | 7.2% | 62.0% |

Note: % is % by mole.

What is claimed is:

1. A process for preparing chlorotrifluoromethylbenzene which comprises reacting chlorotoluene, hydrogen fluoride and chlorine in a gaseous phase in the presence of a catalyst selected from the group consisting of α-aluminum fluoride carrying one or more salts of iron, bismuth, tin and lead, and chromium(III) oxide or partially fluorinated chromium(III) oxide carrying alkali metal fluoride.

2. The process according to claim 1, wherein the catalyst is α-aluminum fluoride carrying one or more salts of iron, bismuth, tin and lead.

3. The process according to claim 2, wherein the amount of the salt carried on 100 g of α-aluminum fluoride is from 0.0005 to 0.05 mole in case of the salt of bismuth or from 0.001 to 0.1 mole in case of the salt of iron, tin or lead.

4. The process according to claim 1, wherein the catalyst is chromium(III) oxide or partially fluorinated chromium(III) oxide carrying alkali metal fluoride.

5. The process according to claim 4, wherein the amount of alkali metal fluoride carried on 100 g of chromium(III) oxide or partially fluorinated chromium(III) oxide is from 0.01 to 0.5 mole.

6. The process according to claim 1, wherein the reaction temperature is from 250° to 450° C.

7. The process according to claim 1, wherein the reaction pressure is from 0.5 to 10 atm.

8. The process according to claim 1, wherein the molar ratio of hydrogen fluoride to chlorotoluene is from 3:1 to 30:1.

9. The process according to claim 1, wherein the molar ratio of chlorine to chlorotoluene is from 3:1 to 20:1.

10. The process according to claim 6, wherein the reaction temperature is from about 350° to about 450° C.

11. The process according to claim 8, wherein the molar ratio of hydrogen fluoride to chlorotoluene is from 4:1 to 20:1.

12. The process according to claim 9, wherein the molar ratio of chlorine to chlorotoluene is from 4:1 to 15:1.

* * * * *